United States Patent [19]
Bouchaudon

[11] 3,969,342
[45] July 13, 1976

[54] DERIVATIVES OF PENICILLANIC ACID AND COMPOSITIONS CONTAINING THEM
[75] Inventor: Jean Bouchaudon, Morsang-Sur-Orge, France
[73] Assignee: Rhone-Poulenc Industries, Paris, France
[22] Filed: Oct. 24, 1975
[21] Appl. No.: 625,503

[30] Foreign Application Priority Data
Oct. 28, 1974 France .............................. 74.35972

[52] U.S. Cl. ............................ 260/239.1; 424/271
[51] Int. Cl.$^2$ ........................................ C07D 499/48
[58] Field of Search .............................. 260/239.1

[56] References Cited
UNITED STATES PATENTS

| | | |
|---|---|---|
| 3,577,408 | 5/1971 | Alburn et al. ..................... 260/239.1 |
| 3,734,904 | 5/1973 | Wendt et al. ..................... 260/239.1 |
| 3,821,198 | 6/1974 | Lee et al. ......................... 260/239.1 |
| 3,873,524 | 3/1975 | Sellstedt et al. .................. 260/239.1 |

Primary Examiner—Gerald A. Schwartz
Attorney, Agent, or Firm—Stevens, Davis, Miller & Mosher

[57] ABSTRACT
Derivatives of penicillanic acid of formula:

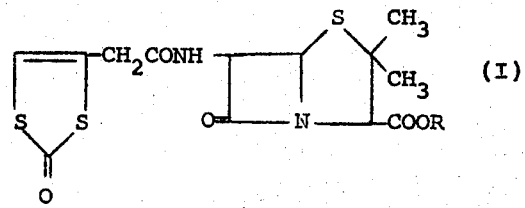

in which R represents hydrogen or a radical of formula:

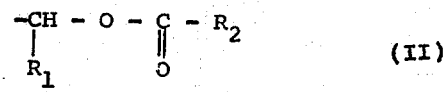

which is easily removable enzymatically, and in which $R_1$ is hydrogen or straight or branched chain $C_{1-4}$ alkyl, phenyl, or phenyl $C_{1-2}$ alkyl and $R_2$ is straight or branched chain $C_{1-4}$ alkyl or alkoxy, cyclohexyl, phenyl or phenyl $C_{1-2}$ alkyl, together with their pharmaceutically acceptable non-toxic metal salts or addition salts with nitrogen-containing bases, have particularly valuable anti-bacterial properties, especially against Gram-positive and Gram-negative bacteria.

6 Claims, No Drawings

DERIVATIVES OF PENICILLANIC ACID AND COMPOSITIONS CONTAINING THEM

The present invention relates to new derivatives of penicillanic acid, to their preparation and to compositions containing them.

The present invention provides derivatives of penicillanic acid of formula:

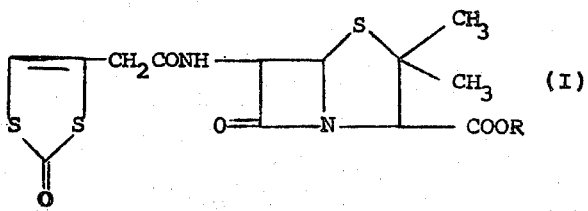

in which R represents hydrogen or a radical which can be easily removed enzymatically, of formula:

in which $R_1$ represents hydrogen or straight or branched chain $C_{1-4}$ alkyl, phenyl or phenyl $C_{1-2}$ alkyl and $R_2$ represents straight or branched chain $C_{1-4}$ alkyl or alkoxy, cyclohexyl, phenyl or phenyl $C_{1-2}$ alkyl, and when R is hydrogen, their pharmaceutically acceptable non-toxic metal salts and addition salts with pharmaceutically acceptable nitrogen-containing bases.

An example of a radical of formula (II) which can be easily removed enzymatically is pivaloyloxymethyl.

According to another aspect of the present invention, the compounds of formula (I) can be prepared by reacting an acid of formula:

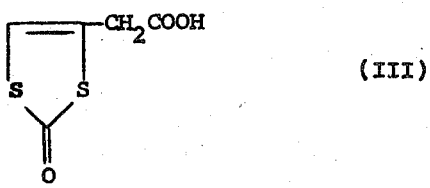

or a reactive derivative of this acid, such as the acid halide, anhydride or a mixed anhydride, with a compound of formula:

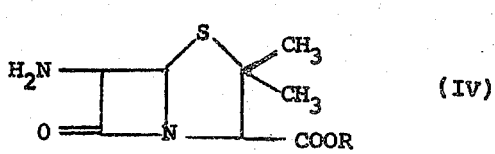

or a salt thereof, in which R is as defined above.

The acid of formula (III) can be reacted either in the presence of a condensation agent such as dicyclohexylcarbodiimide in an organic solvent such as dimethylformamide at a temperature of from −10° to +20°C, or in the form of an acid halide, anhydride or a mixed anhydride, in the presence of an acid acceptor such as a nitrogen-containing organic base, for example triethylamine, in an organic solvent such as chloroform, or in an aqueous-organic medium in the presence of an alkaline condensation agent such as sodium bicarbonate.

The compounds of formula (IV) in which R is a radical of formula (II) can be obtained by esterifying 6-amino-penicillanic acid in accordance with the method described by W. DAEHNE et al., J. Med. Chem. 13, 607 (1970).

The acid of formula (III) can be obtained by cyclising, in an acid medium, an alkyl 4-straight or branched chain $C_{1-4}$ alkoxythiocarbonylthio-3-oxo-butyrate, such as ethyl 4-ethoxythiocarbonylthio-3-oxo-butyrate or ethyl 4-isopropoxythiocarbonylthio-3-oxo-butyrate.

The alkyl 4-alkoxythiocarbonylthio-3-oxo-butyrate can be obtained by reacting a sodium or potassium alkylxanthate with an alkyl γ-haloacetoacetate.

The alkyl γ-haloacetoacetate can be prepared according to A. BURGER and G. E. ULLYOT, J. Org. Chem., 12, 346 (1947).

According to a further aspect of the present invention, derivatives of formula (I), in which R represents a radical of formula (II) as defined above can be prepared by esterifying a derivative of formula (I) in which R represents hydrogen by any method known per se for preparing an ester from a carboxylic acid without affecting the rest of the molecule.

In general, an alkali metal salt or a tertiary amine salt of a derivative of formula (I) is reacted with a halide of formula:

in which $R_1$ and $R_2$ are as defined above and Y represents halogen, preferably in an inert solvent such as dimethylformamide and at a temperature of from 0° to 30°C.

The derivatives of penicillanic acid of formula (I) can optionally be purified by physical methods such as chromatography or crystallisation.

The derivatives of formula (I) in which R represents hydrogen can be converted into metal salts or addition salts with nitrogen-containing bases, by methods known per se, for example either by reacting the derivative of formula (I) with an alkali metal base or an alkaline earth metal base, ammonia or an amine, in a suitable solvent such as an alcohol, an ether, a ketone or water, or by an exchange reaction with a salt of an organic acid. The salt formed precipitates, if necessary after concentrating its solution, and can be isolated by filtration or decantation.

The derivatives of penicillanic acid of formula (I) have particularly valuable antibacterial properties. They exhibit a remarkable activity, in vitro and in vivo, against Gram-positive and Gram-negative bacteria.

In vitro, the derivatives of formula (I) are active at concentrations of between 0.005 and 0.5 μg/cc. against strains of staphylococci which are sensitive to penicillin G (*Staphylococcus aureus* 209 P and *Staphylococcus aureus* Smith), and at concentrations of between 1 to 50 μg/cc. against *Escherichia coli*, Monod strain. They are also active against *Streptococcus pyogenes* and against *Streptococcus pneumoniae* at concentrations of between 0.001 and 0.1 μg/cc., and against *Salmonella typhimurium* at concentrations of between 0.1 and 5 μg/cc.

In vivo, the derivatives of formula (I) are active against experimental infections of mice with *Staphylo-

*coccus aureus* Smith (sensitive to penicillin G) at doses of between 0.01 and 5 mg/kg. per day administered orally or subcutaneously, and with *Escherichia coli* at doses of between 0.1 and 1 mg/kg. per day administered subcutaneously, or of between 0.5 and 30 mg/kg. per day administered orally. They are also active against experimental infections of mice with *Salmonella typhimurium* at doses of between 0.5 and 30 mg/kg. per day administered subcutaneously.

Particularly active derivatives of formula (I) are those in which R represents hydrogen of a radical of formula (II) in which $R_1$ represents hydrogen and $R_2$ represents a straight or branched chain $C_{1-4}$ alkyl.

Especially preferred derivatives of formula (I) are:
6-(1,3-dithiol-2-on-4-yl)-acetamido-penicillanic acid and 3,3-dimethyl-6-[(1,3-dithiol-2-on-4-yl)-acetamido]-7-oxo-2-pivaloyloxymethoxycarbonyl-4-thia-1-azabicyclo[3.2.0]heptane.

The invention is illustrated by the following Examples. Percentages are by weight.

EXAMPLE 1

Triethylamine (14 cc.) is added to a suspension, cooled to −5°C, of 6-amino-penicillanic acid (10.8 g.) in chloroform (250 cc.); a solution of (1,3-dithiol-2-on-4-yl)-acetyl chloride (9.7 g.) in benzene (50 cc.) is then added over the course of 40 minutes. The reaction mixture is then stirred for 30 minutes at −5°C., followed by 1 hour and 45 minutes at 20°C., and is concentrated to dryness under reduced pressure (20 mm. Hg.) at 30°C. The residue thus obtained is dissolved in water (250 cc.). Ethyl acetate (125 cc.) is added and the aqueous phase, cooled to about 0°C, is brought to pH 2 by adding 4 N hydrochloric acid (about 15 cc.). The organic phase is separated off and the aqueous phase is washed with ethyl acetate (twice 100 cc.). The combined organic phases are washed with a saturated sodium chloride solution (4 times 100 cc.) and dried over magnesium sulphate. After filtration, the filtrate is treated with animal charcoal (2 g.), filtered and concentrated to 200 cc. under reduced pressure (20 mm.Hg.) at 30°C. A 2N solution of sodium 2-ethyl-hexanoate in ethyl acetate (20 cc.) is added to the concentrate. A precipitate is obtained, which is kept at 0°C., for 16 hours and is then filtered off and washed with ethyl acetate (3 times 20 cc.) and with ether (3 times 20 cc.). After drying under reduced pressure (0.3 mm.Hg.) at 20°C., the sodium salt of 6-(1,3-dithiol-2-on-4-yl)-acetamido-penicillanic acid (12.1 g.) is obtained; it has the following characteristics: Rf = 0.55 [silica gel; acetone/acetic acid (95/5 by volume)]

$[\alpha]_D^{20} = +254°$ (c = 1.014; water)

Analysis Calculated % : C 39.38; H 3.30; N 7.07; S 24.26; Found : C 39.29; H 3.33; N 7.11; S 23.81.

Infra-red spectrum (determined on potassium bromide tablets) cm$^{-1}$: 3,450, 1,700 and 1,500: amide; 1,775: carbonyl of the β-lactam; 1,615 and 1,410: —COO$^-$; 1,630:

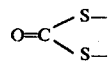

The chloride of (1,3-dithiol-2-on-4-yl)-acetic acid can be prepared in the following manner:

Oxalyl chloride (8.55 cc.) is added, whilst stirring, to a solution of (1,3-dithiol-2-on-4-yl)-acetic acid (8 g.) in ether (100 cc.), which is kept at 20°C. A slight evolution of gas is noted; 5 minutes and 25 minutes after the addition of the oxalyl chloride, dimethylformamide (3 drops) is added. An evolution of gas is observed, which stops after 45 minutes. Decolourising charcoal (1 g.) is then added and the mixture is stirred for 5 minutes. The reaction mixture is filtered; the filtrate is concentrated to dryness under reduced pressure (20 mm.Hg.) at 20°C., taken up in benzene (twice 50 cc.) and concentrated to dryness under the same conditions. This gives (1,3-dithiol-2-on-4-yl)-acetyl chloride (9.7 g.).

(1,3-Dithiol-2-on-4-yl)-acetic acid, can be prepared in the following manner:

80% (by volume) sulphuric acid (500 cc.) is added to ethyl 4-ethoxythiocarbonylthio-3-oxo-butyrate (161 g.) whilst cooling on an ice bath. The temperature rises to 45°C., and the mixture is then heated to 80°C., over the course of 30 minutes. The deep brown solution thus obtained is cooled and then poured onto distilled water (2.5 liters). The mixture is heated for one hour under reflux. It is cooled and extracted with ethyl acetate (4 times 500 cc.) and the organic extracts are washed with distilled water (500 cc.) and extracted with a saturated sodium bicarbonate solution (3 times 500 cc.). The basic fractions are combined and washed with ethyl acetate (500 cc.), and the aqueous phase is acidified to pH 1 with 4 N hydrochloric acid. It is then extracted with ethyl acetate (3 times 500 cc.), the organic phase is washed with distilled water (500 cc.), dried over magnesium sulphate and treated with decolourising charcoal, and the filtrate is concentrated to dryness under reduced pressure (20 mm.Hg). An ochre solid (96 g.) is obtained, which is recrystallised from a mixture of ethyl acetate and cyclohexane (50/50 by volume) (150 cc.). This gives (1,3-dithiol-2-on-4-yl)-acetic acid (68.7 g.) in the form of white crystals melting at 99°C.

Ethyl 4-ethoxythiocarbonylthio-3-oxo-butyrate can be prepared in the following manner:

A suspension of potassium ethylxanthate (160 g.) in ethanol (2 liters) is cooled on an ice bath. A solution of ethyl γ-bromoacetoacetate (209 g.) in ethanol (500 cc.) is added over the course of one hour.

The reactants are left in contact for 16 hours at a temperature of about 20°C, the suspension obtained is then filtered, the precipitate is washed twice with ethanol (100 cc.) and the filtrate is then concentrated to dryness under reduced pressure (20 mm.Hg.). This gives a brown oil (260 g.) which is chromatographed on silica gel (2,000 g.). Elution is carried out with a mixture of ethyl acetate and cyclohexane (5/95 by volume) (6 liters) and then with a mixture of ethyl acetate and cyclohexane (10/90 by volume) (10 liters). These eluates are concentrated under reduced pressure. This gives ethyl 4-ethoxythiocarbonylthio-3-oxo-butyrate (161.2 g.) in the form of an orange oil.

EXAMPLE 2

A solution of (1,3-dithiol-2-on-4-yl)-acetyl chloride (3.88 g.) in benzene (20 cc.) is added dropwise over the course of 20 minutes, whilst stirring, to a solution, cooled to −5°C, of 6-amino-3,3-dimethyl-7-oxo-2-pivaloyloxy-methoxycarbonyl-4-thia-1-aza-bicyclo[3.2.0]-heptane p-toluenesulphonate (10.05 g.) in a mixture of chloroform (100 cc.) and triethylamine (5.6 cc.). The reaction mixture is thereafter stirred for 1 hour and 30 minutes at 20°C, and is then washed successively with water (100 cc.), a 5% sodium bicarbonate solution (twice 100 cc.), 0.1 N iced hydrochloric acid (twice 100 cc.) and water (twice 100 cc.). The organic phase is dried over magnesium sulphate. After filtration and concentration to dryness under reduced pressure (20 mm.Hg) at 30°C, a froth is obtained, which is taken up in methylene chloride (50 cc.). It is chromatographed on a column of silica gel (120 g.) (0.05–0.20 mm, neutral pH; column diameter 2.8 cm, height 44 cm), elution being carried out with methylene chloride and fractions of 100 cc. being collected. Fractions 11 to 26 are combined, and evaporation of these under reduced pressure (20 mm.Hg) at 30°C. gives a froth; on adding ether (100 cc.), this froth dissolves and then solidifies. After standing for two hours in ether, the solid is filtered off and washed with ether (twice 10 cc.) and petroleum ether (twice 10 cc.). After drying under reduced pressure (0.3 mm.Hg) at 20°C, 3,3-dimethyl-6-[(1,3-dithiol-2-on-4-yl)-acetamido]-7-oxo-2-pivaloyloxymethoxycarbonyl-4-thia-1-aza-bicyclo[3.2.0]heptane (3.53 g.) is obtained, having the following characteristics: Rf = 0.34 [silica-gel; chloroform/ethyl acetate (85/15 by volume)] $[\alpha]_D^{20} = +161°$ (c = 1.016; chloroform)

Analysis: Calculated %: C 46.71; H 4.95; N 5.73; S 19.69; Found: C 46.44; H 4.75; N 5.77; S 19.51. Infrared spectrum (determined in solution in bromoform) cm$^{-1}$: 3,410, 1,690 and 1,510: amide; 1.780: carbonyl of the β-lactam; 1,760: ester; 1,100 and 980: —OCH$_2$O—; 1.640:

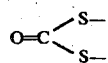

6-Amino-3,3-dimethyl-7-oxo-2-pivaloyloxymethoxycarbonyl-4-thia-1-aza-bicyclo[3.2.0]heptane p-toluenesulphonate can be prepared according to the method described by W. DAEHNE et al., J. Med. Chem. 13, 607 (1970).

The present invention also provides pharmaceutical compositions which are useful for therapeutic purposes, and which contain, as the active ingredient, at least one derivative of formula (I) in association with a pharmaceutically acceptable carrier, diluent or adjuvant. These compositions can be administered orally, parenterally or rectally.

Tablets, pills, powders or granules can be used as solid compositions for oral administration. In these compositions, the active ingredient of the present invention is mixed with one or more inert diluents or adjuvants, such as sucrose, lactose or starch. These compositions can also contain substances other than the diluents, for example a lubricant such as magnesium stearate.

Pharmaceutically acceptable emulsions, solutions, suspensions, syrups and elixirs containing inert diluents such as water or paraffin oil can be used as liquid compositions for oral administration. These compositions can also contain substances other than the diluents, for example adjuvants such as wetting agents, sweeteners or flavouring substances.

The compositions for parenteral administration can be sterile aqueous or non-aqueous solutions, suspensions or emulsions. As the solvent or vehicle, it is possible to employ propylene glycol, polyethylene glycol, vegetable oils, in particular olive oil, and injectable organic esters, for example ethyl oleate. These compositions can also contain adjuvants, in particular wetting agents, emulsifiers or dispersing agents. Sterilisation can be carried out in various ways, for example by a bacteriological filter, by incorporating sterilising agents into the composition, by irradiation or by heating. These compositions can also be prepared in the form of solid sterile compositions which can be dissolved in sterile water or any other sterile injectable medium at the time of use.

The compositions for rectal administration are suppositories which can contain, in addition to the active ingredient, excipients such as cacao butter or suppository wax.

In human therapy, the compositions according to the invention are particularly useful in the treatment of infections of bacterial origin.

In general, the physician will decide the most appropriate posology, taking into consideration the age, the weight, the degree of infection and other factors specific to the subject to be treated. Usually, the dose for an adult patient is between 1 to 12 g. of active ingredient per day, administered orally, intramuscularly or intravenously.

Example 3 which follows illustrates a composition according to the present invention.

EXAMPLE 3

An injectable solution having the following composition is prepared:

| | |
|---|---|
| the sodium salt of 6-(1,3-dithiol-2-on-4-yl)-acetamido-penicillanic acid | 265 mg. |
| sodium chloride | 1.6 mg. |
| injectable solvent | 2 cc. |

I claim:

1. A derivative of penicillanic acid of formula:

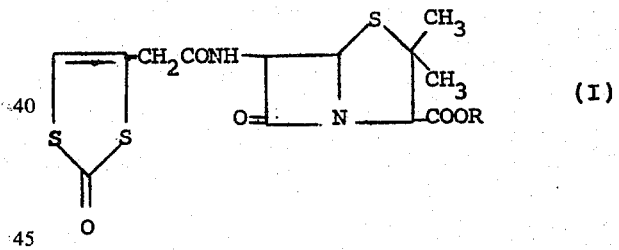

in which R is hydrogen or a radical which can be easily removed enzymatically of formula:

in which $R_1$ is hydrogen or straight or branched chain $C_{1-4}$ alkyl, phenyl or phenyl $C_{1-2}$ alkyl and $R_2$ is straight or branched $C_{1-4}$ alkyl or alkoxy, cyclohexyl, phenyl or phenyl $C_{1-2}$ alkyl, and, when R is hydrogen, its pharmaceutically acceptable non-toxic metal salts and addition salts with pharmaceutically acceptable nitrogen-containing bases.

2. A derivative according to claim 1 in which R is hydrogen or a radical of formula (II) in which $R_1$ is hydrogen and $R_2$ is straight or branched chain $C_{1-4}$ alkyl.

3. A derivative according to claim 2 in which R is pivaloyloxymethyl.

4. A derivative according to claim 1 of formula 6-(1,3-dithiol-2-on-4-yl)-acetamido-penicillanic acid, and its pharmaceutically acceptable salts.

5. A derivative according to claim 1 of formula 3,3-dimethyl-6-[(1,3-dithiol-2-on-4-yl)-acetamido]-7-oxo-2-pivaloyloxymethoxycarbonyl-4-thia-1-aza-bicyclo[3.2.0] heptane.

6. A pharmaceutical composition, which comprises as active ingredient, at least one compound of formula (I) as claimed in claim 1 in association with a pharmaceutically acceptable carrier, diluent or adjuvant.

* * * * *